(12) United States Patent  (10) Patent No.: US 8,757,801 B2
Nakahara et al.  (45) Date of Patent: Jun. 24, 2014

(54) OPHTHALMIC APPARATUS

(75) Inventors: Yasuhiro Nakahara, Kawasaki (JP); Satoshi Aikawa, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 367 days.

(21) Appl. No.: 13/182,781

(22) Filed: Jul. 14, 2011

(65) Prior Publication Data

US 2012/0050670 A1  Mar. 1, 2012

(30) Foreign Application Priority Data

Aug. 31, 2010 (JP) ................................. 2010-195063

(51) Int. Cl.
*A61B 3/10* (2006.01)

(52) U.S. Cl.
USPC .......................................... 351/206; 351/205

(58) Field of Classification Search
USPC ......... 351/205, 206, 208, 209, 211, 212, 221, 351/246
See application file for complete search history.

(56) References Cited

U.S. PATENT DOCUMENTS

| | | | |
|---|---|---|---|
| 3,463,579 A | 8/1969 | Papritz | |
| 4,456,348 A * | 6/1984 | Schulz et al. | 351/212 |
| 5,406,076 A | 4/1995 | Mimura et al. | |
| 5,471,260 A * | 11/1995 | Luce et al. | 351/205 |
| 5,500,696 A | 3/1996 | Masuda et al. | |
| 5,841,502 A * | 11/1998 | Miwa | 351/209 |
| 7,118,561 B2 | 10/2006 | Sugiura | |
| 7,841,717 B2 | 11/2010 | Ito et al. | |
| 2005/0117116 A1 | 6/2005 | Murakami | |
| 2007/0146636 A1 | 6/2007 | Ishikura | |
| 2009/0079939 A1 | 3/2009 | Mimura | |
| 2009/0207378 A1 | 8/2009 | Ito et al. | |
| 2012/0050671 A1 | 3/2012 | Aikawa | |
| 2012/0050672 A1 | 3/2012 | Aikawa | |

FOREIGN PATENT DOCUMENTS

| | | |
|---|---|---|
| CN | 1989894 A | 7/2007 |
| CN | 101190121 A | 6/2008 |
| CN | 101507601 A | 8/2009 |
| JP | 63-300736 A | 12/1988 |
| JP | 01-058232 A | 3/1989 |
| JP | 03-145695 A | 6/1991 |
| JP | 08-203067 A | 8/1996 |
| JP | 3237927 B2 | 12/2001 |
| JP | 2002-010979 A | 1/2002 |

(Continued)

OTHER PUBLICATIONS

Oct. 29, 2013 Chinese Official Action in Chinese Patent Appln. No. 201110239921.X.

*Primary Examiner* — Hung Dang
(74) *Attorney, Agent, or Firm* — Fitzpatrick, Cella, Harper & Scinto

(57) ABSTRACT

An ophthalmic apparatus including an operation stick to adjust an optical unit, comprising: a rotary dial that is provided on a side surface of the operation stick and rotates with respect to the operation stick; a trigger arranged on a top of the operation stick while being decentered with respect to the operation stick; and a control unit adapted to control to perform one of movement and focusing of the optical unit with respect to an object in accordance with rotation of the rotary dial and perform control to cause the optical unit to start a predetermined operation in accordance with press of the trigger.

20 Claims, 10 Drawing Sheets

(56) References Cited

FOREIGN PATENT DOCUMENTS

| JP | 3244873 | B2 | 1/2002 |
| JP | 2003-235803 | A | 8/2003 |
| JP | 2006-130227 | A | 5/2006 |
| JP | 2008-054929 | A | 3/2008 |
| JP | 2009-072513 | A | 4/2009 |

\* cited by examiner

OPHTHALMIC APPARATUS

BACKGROUND OF THE INVENTION

1. Field of the Invention

The present invention relates to an ophthalmic apparatus to be used in an ophthalmic clinic, a hospital, and the like.

2. Description of the Related Art

A Joystick mechanism is commonly used to operate ophthalmic apparatus. Japanese Patent Laid-Open No. 01-058232 discloses a mechanism in an ophthalmic apparatus such as a fundus camera, which has a vertical movement knob that is arranged around the lower portion of a joystick, is mechanically linked to a screw mechanism on the lower side of an optical unit; by rotation of the vertical movement knob the optical unit is moved in the vertical direction. Japanese Patent No. 3244873 discloses providing a jog dial near the joystick of an ophthalmic apparatus such as a fundus camera and performing settings in accordance with various modes such as changing the illumination light amount by rotating the jog dial.

The mechanism disclosed in Japanese Patent Laid-Open No. 01-058232 improves operability by mechanically moving the optical unit in the vertical direction. However, in accordance with the weight of the optical unit, this mechanical system requires a large force when operating the vertical movement knob. For this reason, the burden on the operator is heavy. In Japanese Patent No. 3244873, the jog dial is provided near the joystick. However, after moving the optical unit leftward or rightward using the joystick, the operator must again place a hand on the jog dial to change the illumination light amount. For this reason, operability is poor. Note that neither Japanese Patent Laid-Open No. 01-058232 nor Japanese Patent No. 3244873 include any disclosure regarding focusing.

Considering the above-described problems, the present invention is directed to improve operability of the ophthalmic apparatus, and enable a series of operations including alignment, focusing, and shooting without changing the grip position of the joystick.

SUMMARY OF THE INVENTION

According to one aspect of the present invention, there is provided an ophthalmic apparatus including an operation stick to adjust an optical unit, comprising: a rotary dial that is provided on a side surface of the operation stick and rotates with respect to the operation stick; a trigger arranged on a top of the operation stick while being decentered with respect to the operation stick; and a control unit adapted to control to perform one of movement and focusing of the optical unit with respect to an object in accordance with rotation of the rotary dial and perform control to cause the optical unit to start a predetermined operation in accordance with press of the trigger.

Further features of the present invention will be apparent from the following description of exemplary embodiments with reference to the attached drawings.

DESCRIPTION OF THE EMBODIMENTS

Exemplary embodiments of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

The schematic arrangement of a fundus shooting apparatus according to the first embodiment will be described with reference to FIGS. 1A to 3.

Figure 1A:
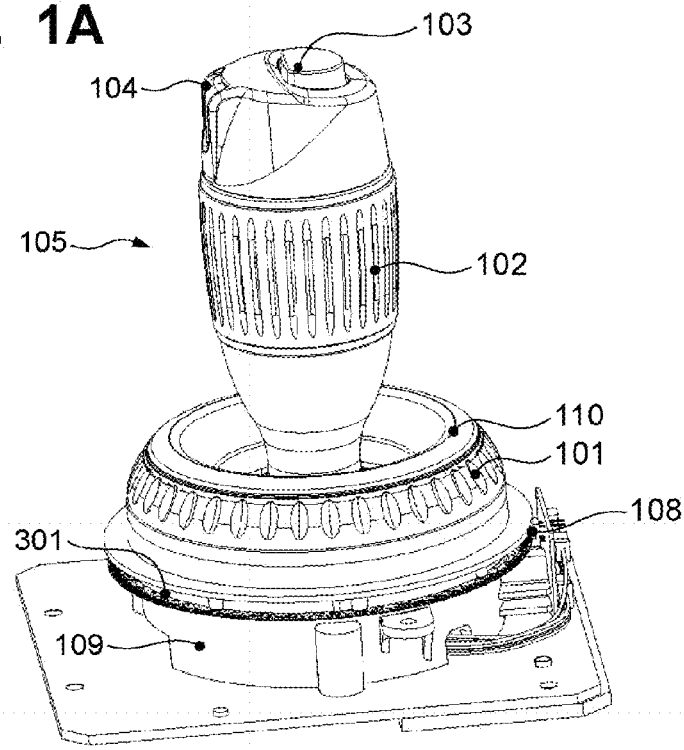
FIG. 1A is a view showing an example of a joystick portion 105 that constitutes part of a fundus shooting apparatus.
Figure 3:
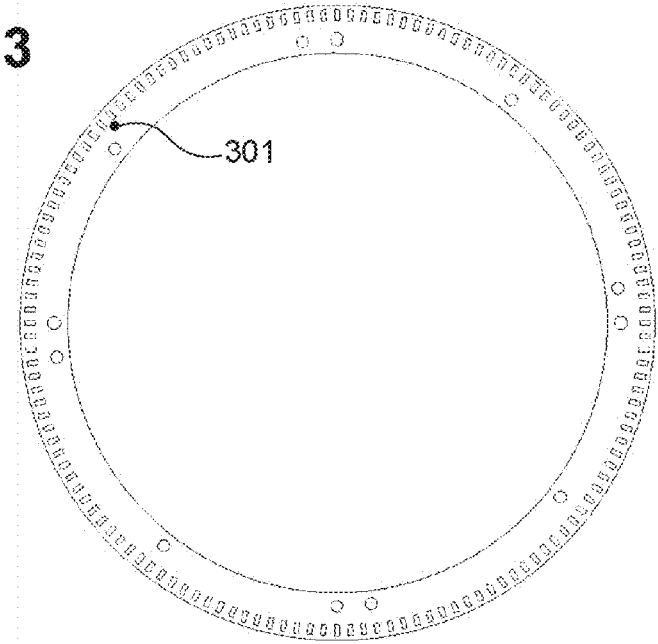
FIG. 3 is a view showing the schematic mechanical structure of the fundus shooting apparatus.

A joystick portion 105 that constitutes the joystick mechanism of the fundus shooting apparatus will now be described first with reference to FIG. 1A. The joystick portion 105 includes a focus dial 101 (a second rotary dial serving as a second rotary member) and a vertical movement dial 102 (a first rotary dial serving as a first rotary member). The joystick portion 105 also includes a shooting button 103, an anterior alignment switching button 104, a photo interrupter 108, a focus dial base portion 109, a locking member 110, and a slit plate 301 whose details are illustrated in FIG. 3.

The operator rotates the focus dial 101 to adjust the focus of the electric focusing mechanism that is the operation target. The focus dial 101 is arranged on the focus dial base portion 109 (supporting member) that supports the rotary dial. The supporting member is arranged at one end of the focus dial 101. Note that the supporting member may be integrated with the joystick portion 105 or formed as a separate member. The focus dial 101 may be arranged on the operation stick or on the supporting member so as to be coaxial with respect to the central axis of the operation stick in the longitudinal direction. The focus dial 101 may be arranged on the supporting member so as to be coaxial with respect to the central axis of the operation stick in the longitudinal direction under the standard condition without tilt of the operation stick.

Figure 2A:
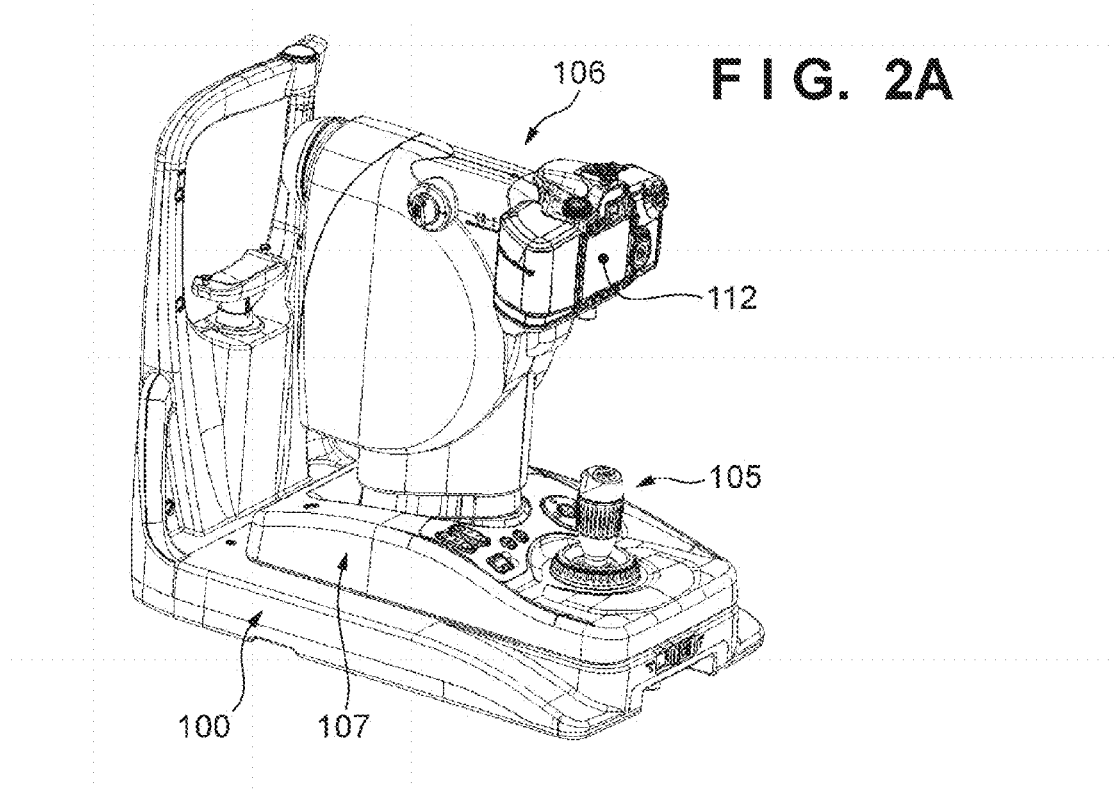
FIG. 2A is a view showing the schematic mechanical structure of the fundus shooting apparatus.

The operator rotates the vertical movement dial 102 to move an optical unit 106 shown in FIG. 2A in the vertical direction. The vertical movement dial 102 is arranged on the operation stick. The shooting button 103 is a pressible button. When the operator presses the shooting button 103, shooting starts.

Figure 1B:
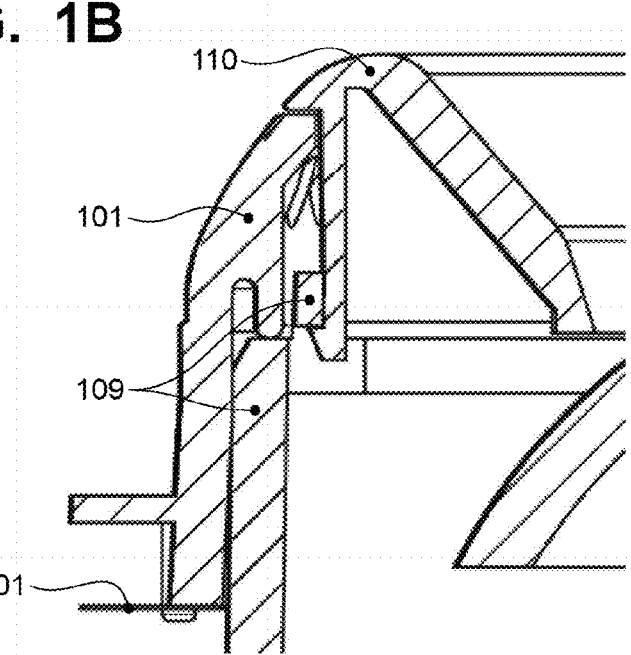
FIG. 1B is a sectional view showing part of the joystick portion 105.

The anterior alignment switching button 104 (anterior observation switching button) is a pressible button. The operator can insert or remove an anterior observation lens 520 to be described later with reference to FIG. 5 by pressing the anterior alignment switching button 104. The photo interrupter 108 is an element that packages an infrared light source and an infrared light-receiving element (neither are shown). After the slit plate 301 has been fixed to the focus dial 101, the focus dial 101 is pivotally fitted on the focus dial base portion 109. The focus dial base portion 109 then functions to hold the mounted substrate such that the slit plate 301 passes between the infrared light source portion and the infrared light-receiving element (neither are shown) of the photo interrupter 108. The locking member 110 prevents the focus dial 101 from being disconnected from the focus dial base portion 109 (supporting member), and engages with the focus dial base portion 109, as shown in FIG. 1B. Note that the locking member 110 is arranged on the focus dial 101 (on the second rotary member). However, any other structure can be adopted as far as the locking member 110 is arranged to separate the focus dial 101 from the vertical movement dial 102.

The focus dial 101 is simply fitted on the focus dial base portion 109 but not linked with other mechanical components. Hence, for example, a testing technician can easily operate the focus dial 101 using the little finger.

An example of the arrangement of the fundus shooting apparatus will be described with reference to FIG. 2A. The fundus shooting apparatus includes, for example, a base portion 100, the joystick portion 105, the optical unit 106, a stage portion 107, and a display unit 112.

The optical unit 106 can be driven in the vertical direction by the vertical movement dial 102 described with reference to FIG. 1A. The stage portion 107 freely moves on the base portion 100. The joystick portion 105 is arranged on the stage portion 107. The operator can slightly move the stage portion 107 by tilting the operation stick of the joystick portion 105. When the stage portion 107 moves, the optical unit 106 can move in the two-dimensional plane in the back-and-forth direction or the horizontal direction, distinct from the vertical direction. The display unit 112 displays an observed image or a shooting result.

Figure 2B:
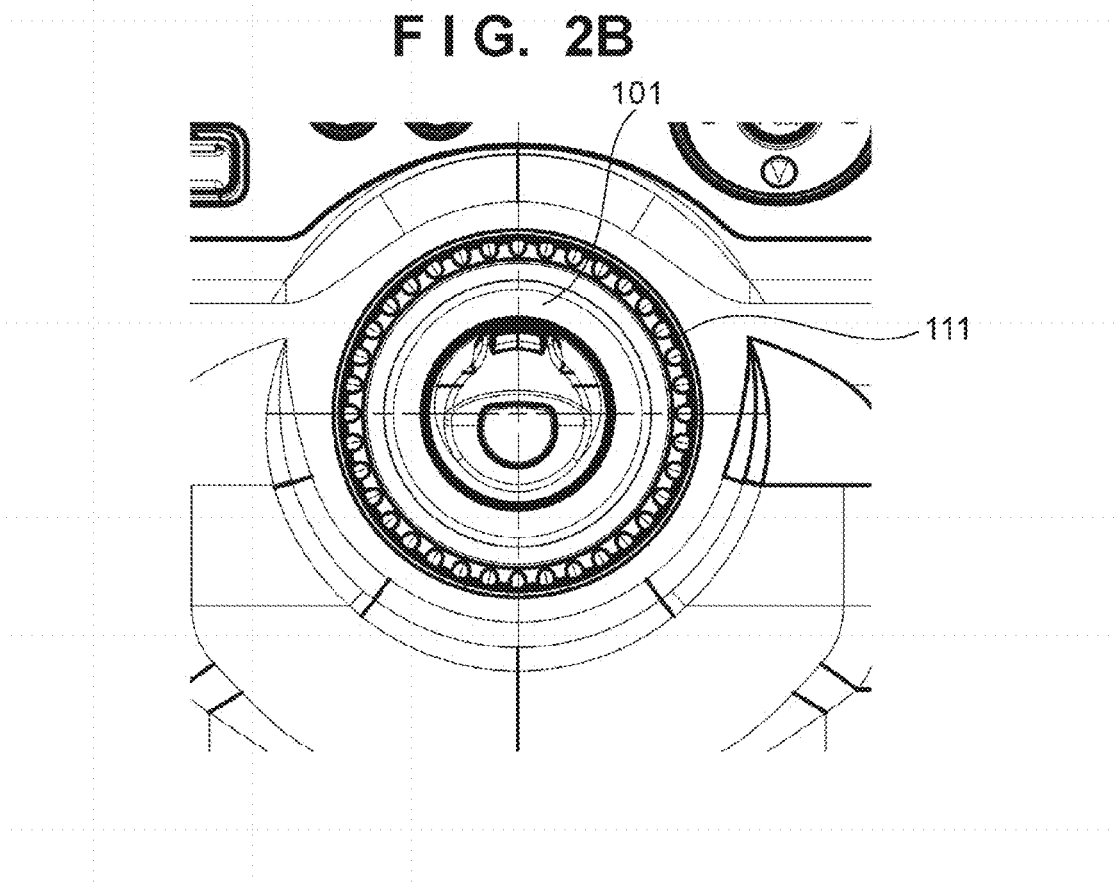
FIG. 2B is an upper view of the joystick portion 105.

As shown in FIG. 2B, the focus dial 101 is arranged at almost the center of a hole 111 having, for example, a circular shape to make the joystick portion 105 project from the outer cover. This position corresponds to the substantial center of the joystick portion 105 placed at the central position.

Figure 4:
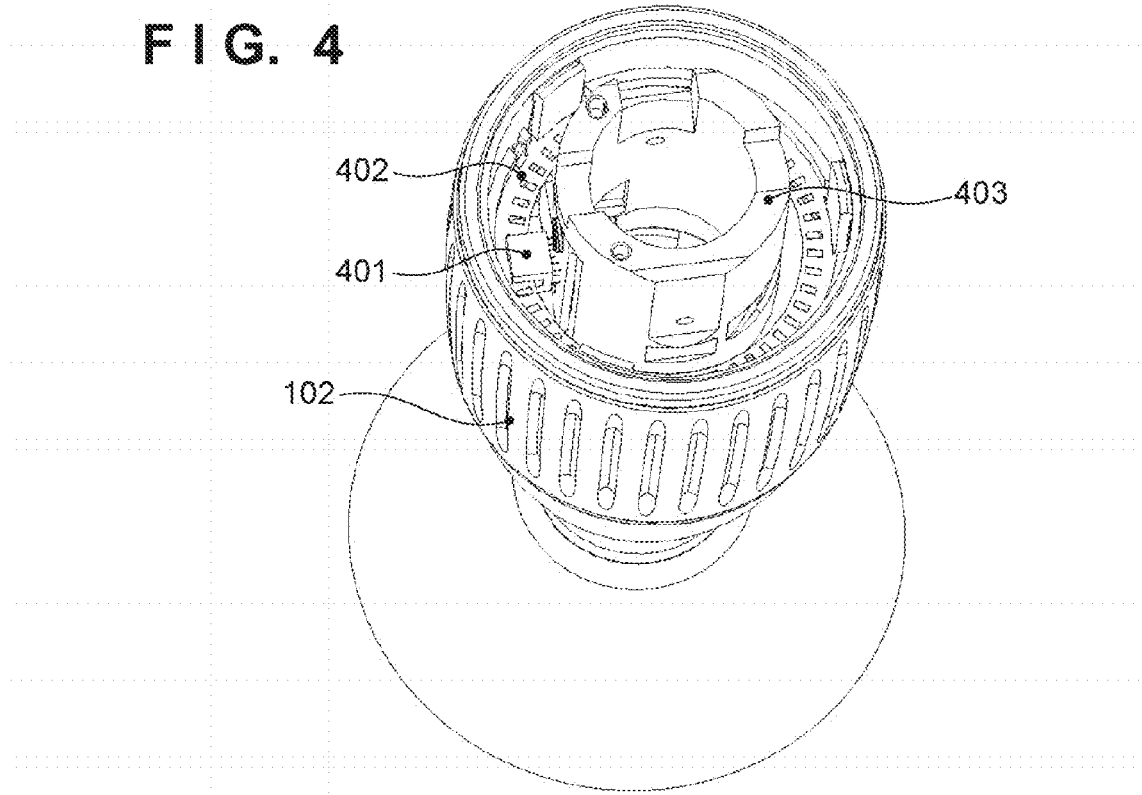
FIG. 4 is a perspective view showing the internal structure of the operation stick of the joystick portion 105.

An example of the internal structure of the operation stick of the joystick portion 105 will be explained with reference to FIG. 4. A photo interrupter 401 is identical to the photo interrupter 108. An optical vertical movement dial base 403 is the base portion of the vertical movement dial 102 that moves the optical unit 106 in the vertical direction. The photo interrupter 401 is fixed to the optical vertical movement dial base 403. When the vertical movement dial 102 pivots, a slit plate 402 passes between the infrared light source portion and the infrared light-receiving element of the photo interrupter 401. The slit plate 402 is fixed to the vertical movement dial 102 of the optical unit 106. The vertical movement dial 102 pivots around the optical vertical movement dial base 403.

A schematic block diagram of the fundus shooting apparatus according to the first embodiment will be described with reference to FIG. 5. An infrared LED light source 501 is the light source to be used to observe the fundus of an object by infrared light. A light source 502 is a white LED light source or a visible light source to be used to visibly shoot the fundus of the object.

An infrared ring slit 505 is a mask that changes illumination light from the infrared LED light source 501 into ring illumination. A capacitor C supplies power to the white LED light source 502. The amount of charge stored in the capacitor C changes depending on the shooting mode. The capacitor C is appropriately charged or discharged each time the shooting mode changes. The charge/discharge control is performed by a system control unit 522 to be described later.

The system control unit 522 performs drive control of driving units M1 to M5, control of detection units S1 to S7, control based on input from the user interface, and control of image data processing and processing for displaying an obtained image on the display unit 112. The driving unit M4 inserts/removes the white LED light source 502 and the infrared LED light source 501 onto/from an illumination optical path O1 to be described later. The position detection unit S4 detects positions of the white LED light source 502 and the infrared LED light source 501. In the observation mode, the infrared LED light source 501 is inserted onto the illumination optical path O1. When the operator presses the shooting button 103 of the joystick to send a trigger signal (not shown) to the system control unit 522, the light source changes from the infrared LED light source to the white LED light source 502. After that, the light source changes to the infrared LED light source 501 again. The white LED light source 502 and the infrared LED light source 501 go off when the system control unit 522 determines that observation has not been performed for a predetermined time. The ring illumination forms an image on an object 512 through an illumination relay lens 507 and an illumination relay lens 509.

Figure 5:
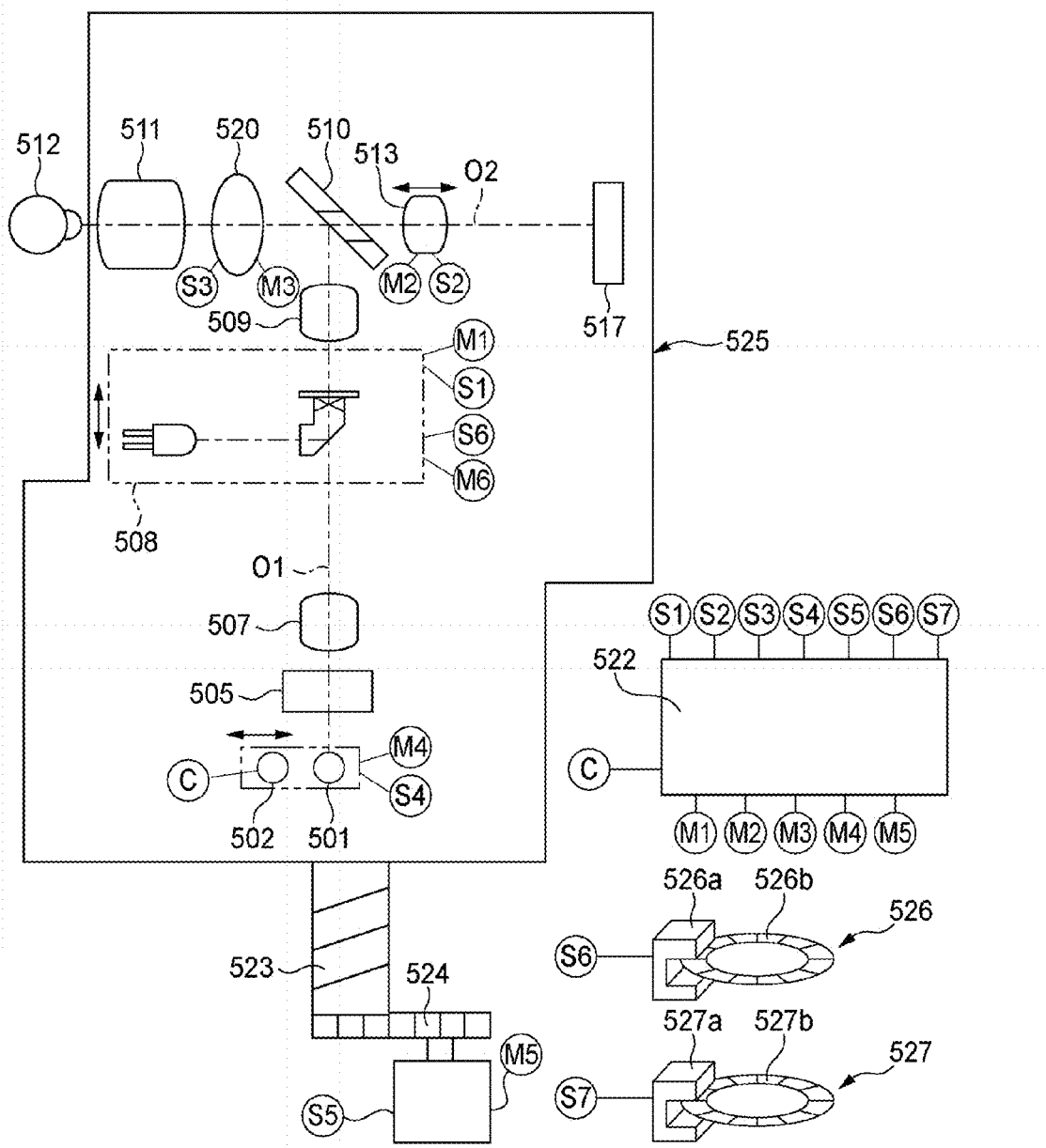
FIG. 5 is a schematic block diagram of the fundus shooting apparatus according to the first embodiment.

A split unit 508 includes a light source configured to project a focus indicator, a moving mechanism that enters the illumination optical path O1 and moves in the direction of the arrow in FIG. 5 to move the focus indicator in the optical axis direction in the observation mode, and a retracting mechanism that retracts the unit from an illumination optical path O2 in the shooting mode. The split driving motor M1 drives the split unit 508 to adjust the focal point of the focus indicator, and the split position detection unit S1 detects the stop position of the split unit 508. In addition, the driving unit M6 drives the split unit 508 in the direction of the arrow in FIG. 5, and the position detection unit S6 detects the position of the split unit 508 at that time.

A perforated mirror 510 is a total reflection mirror having a hole at the center, which is configured to reflect ring illumination by the outer mirror and pass shooting light through the hole at the center. The ring illumination that has passed through the perforated mirror 510 forms an image on the object 512 through an objective lens 511 and illuminates the object 512. The reflected light forms an image at the center of the perforated mirror 510 through the objective lens 511. The shooting optical axis O2 runs from the image of the fundus of the object to an imaging sensor 517.

When the anterior observation lens 520 is inserted into the shooting optical axis O2, the anterior ocular segment can be observed. On the other hand, when the anterior observation lens 520 is not inserted into the shooting optical axis O2, the fundus can be observed. Insertion/removal of the anterior observation lens 520 into/from the shooting optical axis O2 is done using the anterior observation lens driving motor M3 and the anterior observation lens position detection unit S3. Upon receiving a trigger signal (not shown) generated by pressing the anterior alignment switching button 104 of the joystick portion 105, the system control unit 522 executes switching control of the anterior observation lens 520.

The imaging sensor 517 photoelectrically converts the shooting light. An electrical signal obtained by photoelectric conversion is converted into digital data by the system control unit 522. In the infrared observation mode, the observed image is displayed on the display unit 112. In the shooting mode, the observed image is recorded in a recording medium (not shown). A focus lens 513 is used to adjust the focus of the shooting light beam that has passed through the hole at the center of the perforated mirror 510. The focus lens 513 moves in the direction of the arrow in FIG. 5 to adjust focus. The focus lens driving motor M2 drives the focus lens 513 based on a pulse from the system control unit 522. The position detection unit S2 detects the position of the focus lens 513.

When the testing technician operates the focus dial 101 of the joystick portion 105, the slit plate 301 passes between the infrared light source portion and the infrared light-receiving element of the photo interrupter 108. A focusing encoder unit 527 sends two pulse signals (not shown) of different timings to the system control unit 522 through detection unit S7. The system control unit 522 can detect the rotational direction and the rotating speed from the shift between the two pulses. The system control unit 522 aligns the focus motor and adjusts it to a desired focus state.

A photo interrupter 527a corresponds to the photo interrupter 108 in FIG. 1. A slit plate 527b corresponds to the slit plate 301 in FIG. 1.

An optical unit 525 is a portion corresponding to the optical unit 106. A feed screw portion 523 is a screw portion that moves the optical unit 525 in the vertical direction by the driving unit M5. A gear portion 524 is fitted and fixed on the shaft of the driving unit M5 to pivot the feed screw. The feed screw portion 523, the driving unit M5, and the gear portion 524 are arranged on the stage portion 107. The position detection unit S5 detects a position of the optical unit 525.

When the testing technician operates the vertical movement dial 102 of the joystick portion 105, the slit plate 402 passes between the infrared light source portion and the infrared light-receiving element of the photo interrupter 401. An optical unit alignment adjusting encoder unit 526 sends two pulse signals (not shown) of different timings to the system control unit 522 through detection unit S6. The system control unit 522 can detect the rotational direction and the rotating speed from the shift between the two pulse signals. The system control unit 522 aligns the optical unit 106 in the vertical direction and sets it to a desired height by adjusting its driving direction and driving speed. A photo interrupter 526a corresponds to the photo interrupter 108 in FIG. 1. A slit plate 526b corresponds to the slit plate 301 in FIG. 3.

Since the focus dial 101 and the vertical movement dial 102 are arranged close to each other (the focus dial 101 is arranged around the lower portion of the joystick), the operator may erroneously operate these operation members simultaneously. In this embodiment, the locking member 110 of the focus dial 101 has the same locking shape as the shape of the upper surface of the focus dial 101. This makes it possible to prevent the operator from erroneously operating the focus dial 101 when operating the vertical movement dial 102 above the focus dial 101. Note that the functions of the dials 101 and 102 may be changed appropriately in accordance with their respective purposes. For example, the dial 101 may be configured for vertical movement, and the dial 102 may be configured for focusing.

(Arrangement Positions and Shapes of Vertical Movement Dial 102 and Shooting Button 103)

If the operation members are concentrated onto the joystick to reduce the required number of operator hand movements and thus improve operability, an operator, who is going to operate a certain operation member, may simultaneously operate an unwanted operation member at higher probability. This means that the apparatus may perform an (erroneous) operation not intended by the operator at higher probability.

U.S. Pat. No. 5,406,076 discloses a joystick mechanism that includes a rotating knob with an operation button (a button for shooting) provided on the top to generate a trigger signal. Since the operation button is arranged on the top of the rotating knob, the operator may rotate the rotating knob unintentionally when operating the operation button. This makes the optical unit move in the vertical direction after completion of alignment. Consequently, re-shooting is required.

Since the rotating knob disclosed in U.S. Pat. No. 5,406,076 has the operation button on its top, the operation button may rotate together with the rotating knob. Hence, the operation button is practically formed as a circular operation member at the center of the rotating knob. If the operation button is decentered or formed into a non-circular shape, the position of the operation button moves as the rotating knob rotates.

On the other hand, the vertical movement dial 102 of the fundus shooting apparatus according to this embodiment is arranged in the middle of the joystick. Even when the vertical movement dial 102 rotates, the upper portion of the joystick does not move in synchronism and remains fixed. The shooting button 103 and the anterior alignment vertical switching button 104 are arranged on the upper fixed portion of the joystick. The shooting button 103 and the anterior alignment switching button 104 are arranged at the end of the operation stick at a predetermined distance away from the rotary member, and hold the arranged states without moving in synchronism with the rotation of the rotary member. The shooting button 103 and the anterior alignment switching button 104 hold a positional relationship such that it is guaranteed that when the testing technician lightly grips the vertical movement dial 102 of the joystick with the thumb, the middle finger, and the third finger, the index finger naturally sits atop the shooting button 103. On the joystick having the size of this embodiment, the shooting button 103 is arranged at a position slightly offset from the center toward the testing technician (a position at a predetermined distance away from the central axis of rotation). The shooting button 103 and its periphery have shapes that allow the tip of the index finger to naturally sit on the button and perform the press-in operation.

The anterior alignment switching button 104 is arranged on the opposite side with respect to the testing technician such that he/she can press the button without moving the hand off the joystick but only by consciously stretching the finger with the intent of pressing the button. In addition, a bank portion is formed around the button to prevent unwanted transition between the anterior observation mode and the fundus shooting mode. The dial for rotation and the button for shooting can thus be arranged so that the operator rarely suffers an operation error. In addition, the arrangement and shape of the shooting button can be designed to obviate the necessity on the part of the operator to change the grip position.

Second Embodiment

The second embodiment is different from the first embodiment only in the arrangement of the focus dial and the optical vertical movement dial on the joystick, and the control method of the system control unit. Hence, mainly the different points will now be described with reference to FIGS. 6 to 9.

Figure 6:
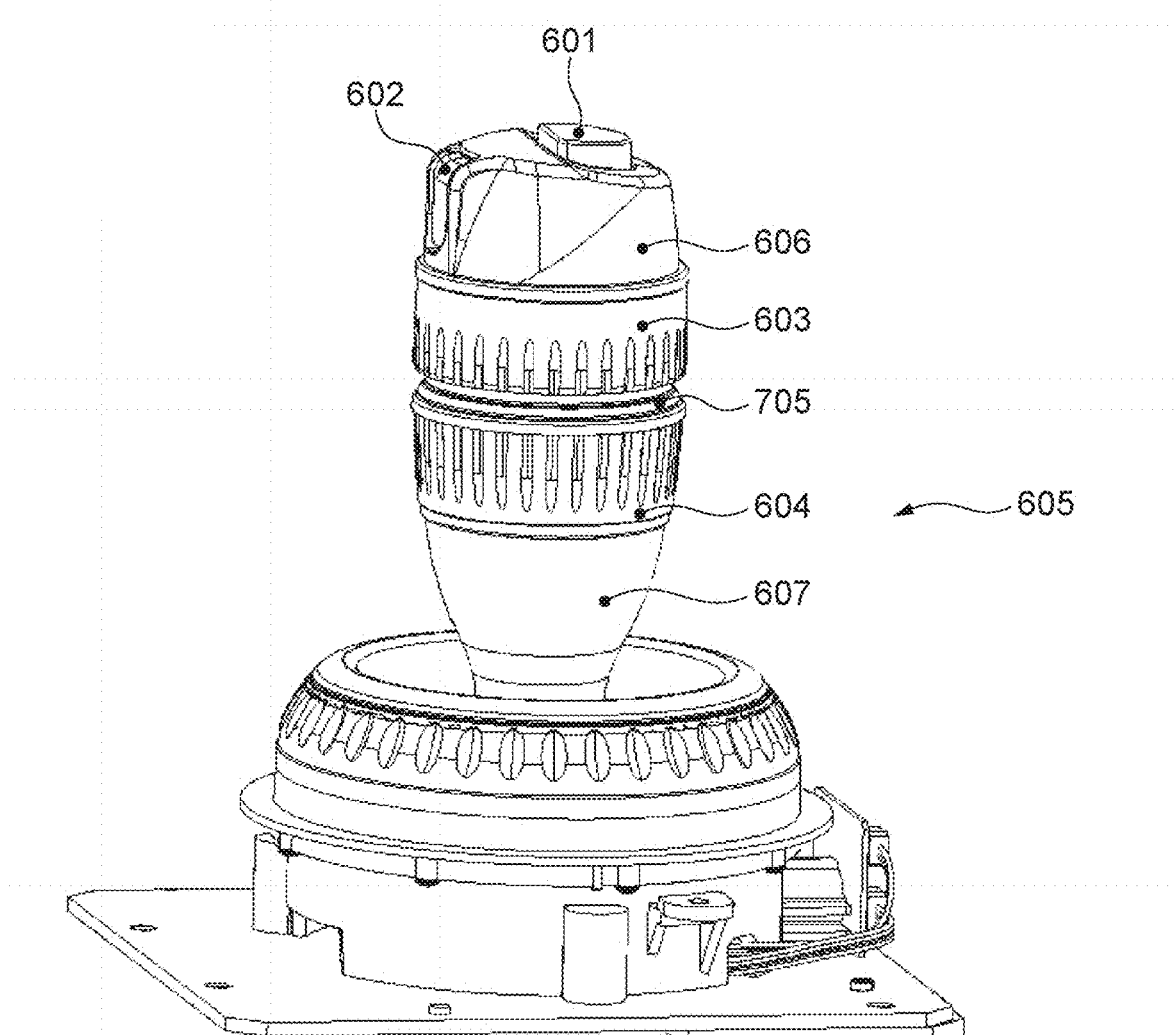
FIG. 6 is a view showing an example of a joystick portion 605 that constitutes part of a fundus shooting apparatus.

A joystick portion 605 according to the second embodiment will be described with reference to FIG. 6. The joystick portion 605 includes a shooting button 601, an anterior alignment switching button 602, an optical vertical movement dial 603, a focus dial 604, a top cover 606, a lower cover 607, and a dial strut 705 that is also illustrated in FIG. 7.

The optical vertical movement dial 603 has the same function as that of the vertical movement dial 102 described in the first embodiment. The optical vertical movement dial 603 pivots almost coaxially with the joystick portion 605. The optical vertical movement dial 603 has an almost hollow cylindrical shape and is pivotally fitted on the dial strut 705, as shown in FIG. 7. The top cover 606 engages with the dial strut 705 to prevent the optical vertical movement dial 603 from being disconnected.

The focus dial 604 has the same function as that of the focus dial 101 described in the first embodiment. The focus dial 604 pivots almost coaxially with the joystick portion 605. The focus dial 604 has an almost hollow cylindrical shape and is pivotally fitted on the dial strut 705, as shown in FIG. 7. The member engages with the lower cover 607 so as not to be disconnected. The top cover 606 holds the shooting button 601 and the anterior alignment switching button 602.

Figure 7:
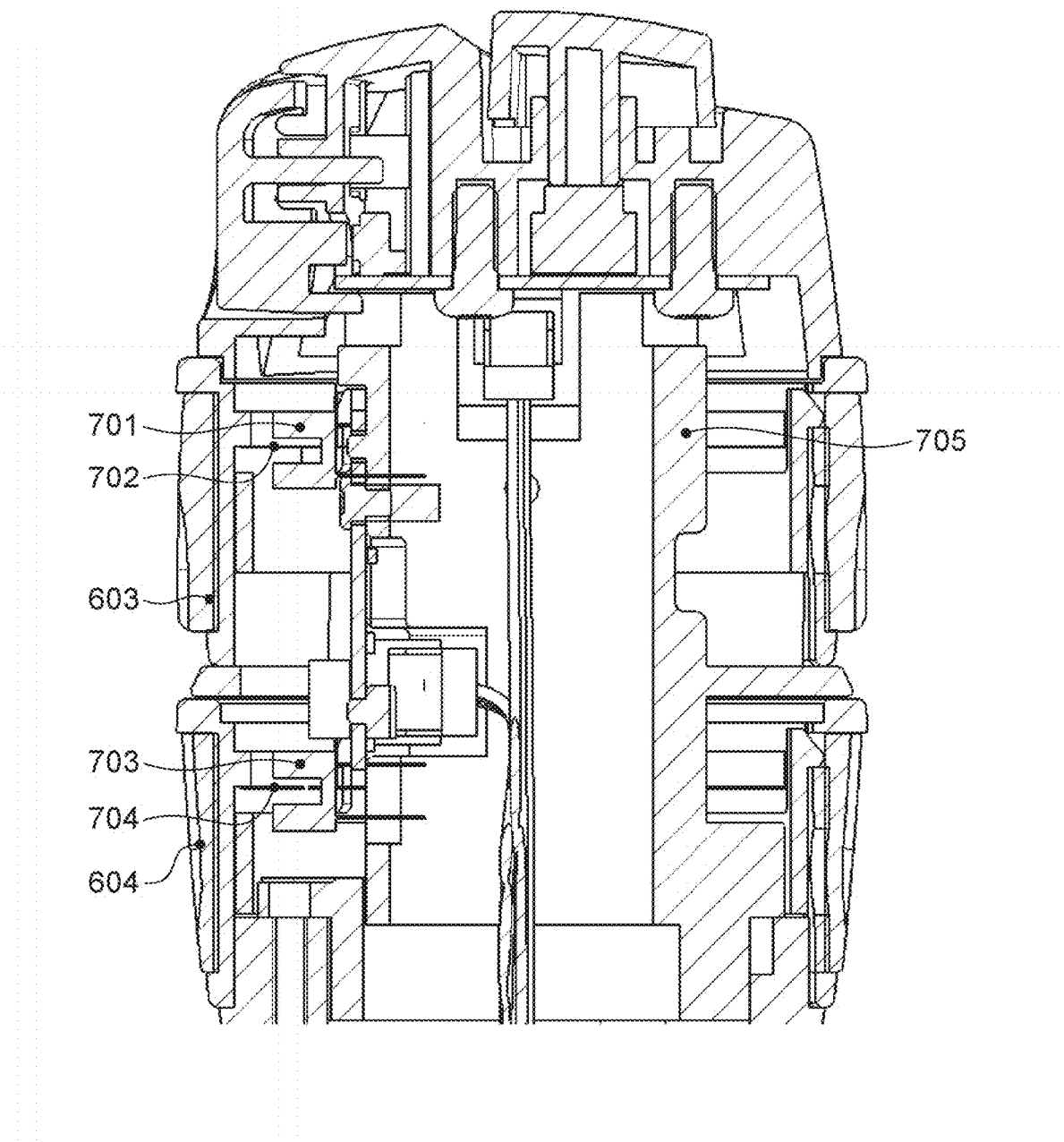
FIG. 7 is a sectional view of the operation stick of the joystick portion 605.

Referring to FIG. 7, a photo interrupter 701 has the same function as that of the photo interrupter 108. A slit plate 702 is the same as the slit plate 402. The slit plate 702 is fixed to the optical vertical movement dial 603. When the optical vertical movement dial 603 pivots, the slit plate 702 similarly pivots and passes between the light source portion and the light-receiving portion (neither are shown) of the photo interrupter 701. Two pulses (not shown) in different phases are sent to a system control unit 801. The system control unit 801 detects the rotation and aligns an optical unit 525. A photo interrupter 703 has the same function as that of the photo interrupter 108. A slit plate 704 is the same as the slit plate 402. The slit plate 704 is fixed to the focus dial 604. When the focus dial 604 pivots, the slit plate 704 similarly pivots and passes between the light source portion and the light-receiving portion (neither are shown) of the photo interrupter 703. Two pulses (not shown) in different phases are sent to the system control unit 801. The system control unit 801 detects the rotation and aligns a focus lens 513.

Since the focus dial 604 and the optical vertical movement dial 603 are arranged close to each other, an operation error may occur. Upon detecting operation of one dial, the system control unit 801 disables any operation of the rotary dials other than the rotary dial under operation.

Figure 8:
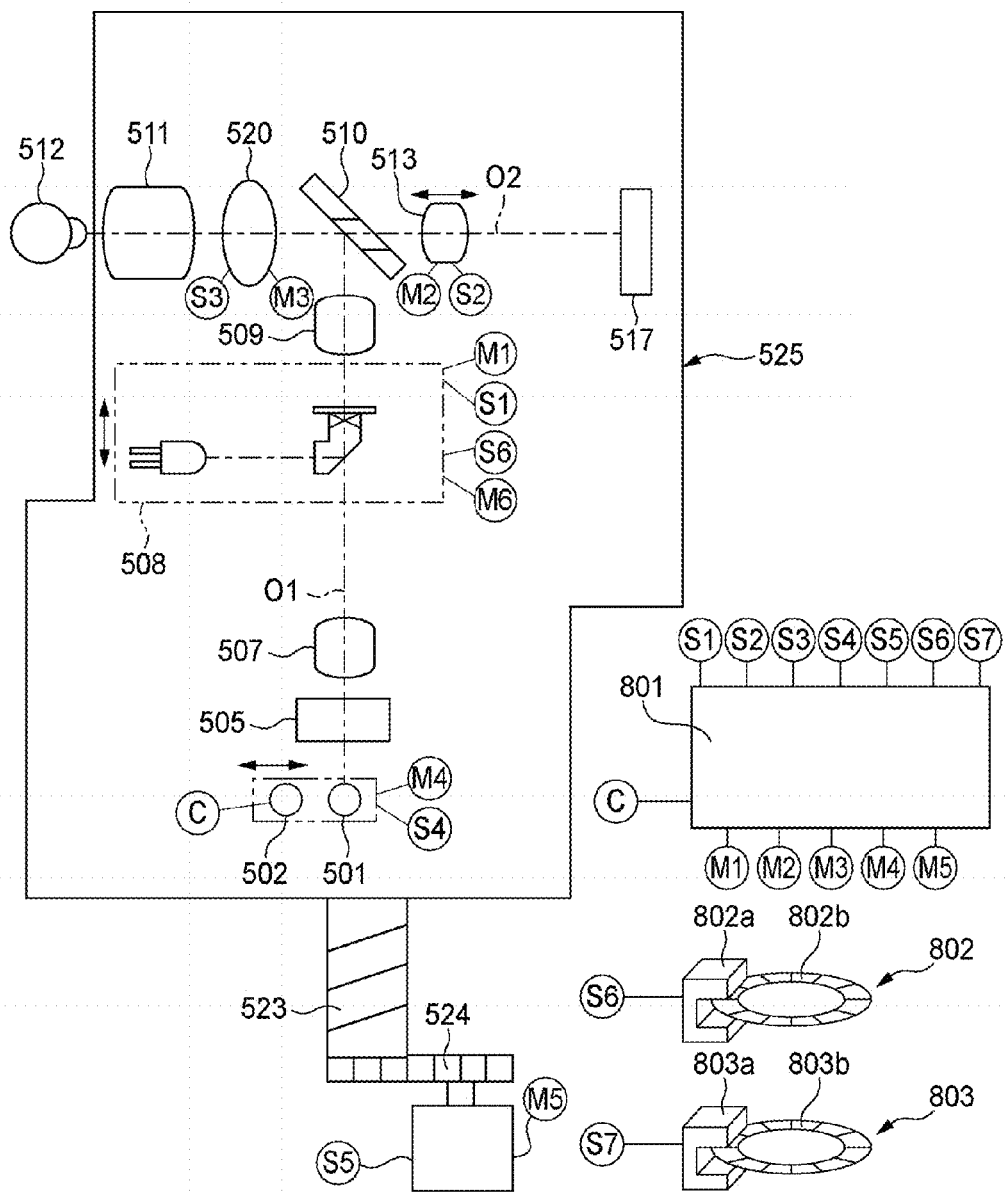
FIG. 8 is a schematic block diagram of a fundus shooting apparatus according to the second embodiment.

A schematic block diagram of a fundus shooting apparatus according to the second embodiment will be described with reference to FIG. 8. When the testing technician operates the optical vertical movement dial 603 of the joystick portion 605, the slit plate 702 in FIG. 7 passes between the infrared light source portion and the infrared light-receiving element of the photo interrupter 701. An optical unit alignment adjusting encoder unit 802 in FIG. 8 sends two pulse signals (not shown) of different timings to the system control unit 801 through the detection unit S6. The system control unit 801 can detect the rotational direction and the rotating speed from the shift between the two pulse signals. The system control unit 801 aligns the optical unit 525 in the vertical direction and sets it to a desired height by adjusting its driving direction and driving speed. A photo interrupter 802a corresponds to the photo interrupter 701 in FIG. 7. A slit plate 802b corresponds to the slit plate 702 in FIG. 7.

When the testing technician operates the focus dial 604 of the joystick portion 605, the slit plate 704 passes between the infrared light source portion and the infrared light-receiving element of the photo interrupter 703. A focusing encoder unit 803 sends two pulse signals (not shown) of different timings to the system control unit 801 through the detection unit S7. The system control unit 801 can detect the rotational direction and the rotating speed from the shift between the two pulses. The system control unit 801 aligns the focus motor and adjusts it to a desired focus state. A photo interrupter 803a corresponds to the photo interrupter 703 in FIG. 7. A slit plate 803b corresponds to the slit plate 704 in FIG. 7.

Figure 9:
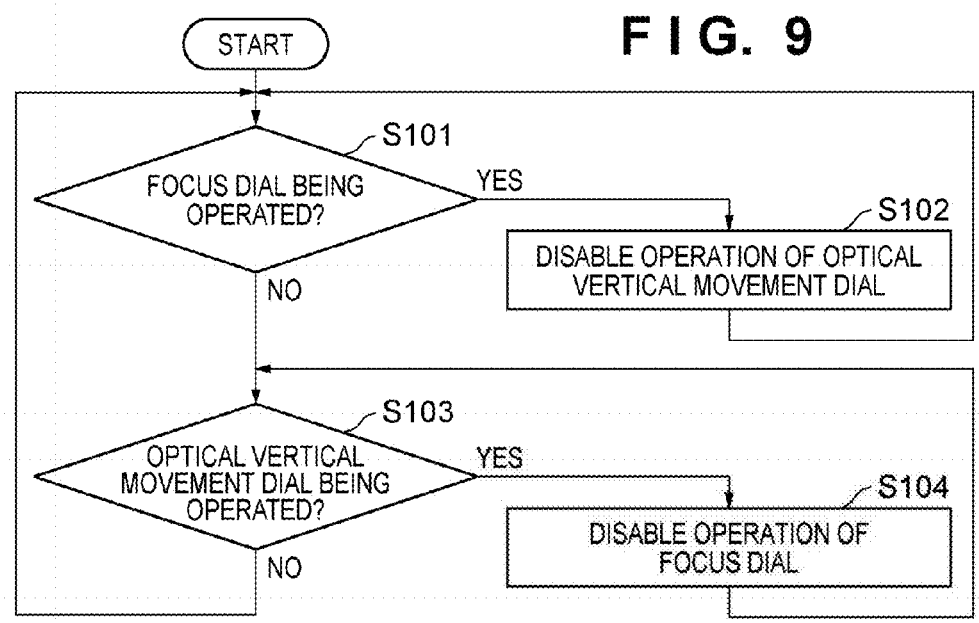
FIG. 9 is a flowchart illustrating the procedure of processing of disabling the operation of a rotary dial.

The procedure of processing for disabling the operation of a rotary dial will now be described with reference to the flowchart of FIG. 9.

In step S101, it is determined whether the focus dial 604 is being operated. Whether the focus dial 604 is being operated is determined by causing the system control unit 801 to detect whether the encoder unit 803 is sending a pulse signal. Upon determining that the focus dial 604 is being operated (YES in step S101), the process advances to step S102. Upon determining that the focus dial 604 is not being operated (NO in step S101), the process advances to step S103.

In step S102, the system control unit 801 neglects the pulse signal sent from the optical unit alignment adjusting encoder unit 802 of the optical vertical movement dial 603. More specifically, the system control unit 801 does not accept the pulse signal. After that, the process returns to step S101.

In step S103, it is determined whether or not the optical vertical movement dial 603 is being operated. Whether or not the optical vertical movement dial 603 is being operated is determined by causing the system control unit 801 to detect whether the optical unit alignment adjusting encoder unit 802 is sending a pulse signal. Upon determining that the optical vertical movement dial 603 is being operated (YES in step S103), the process advances to step S104. Upon determining that the optical vertical movement dial 603 is not being operated (NO in step S103), the process returns to step S101.

In step S104, the system control unit 801 neglects the pulse signal sent from the encoder unit 803 of the focus dial 604. More specifically, the system control unit 801 does not accept the pulse signal. After that, the process returns to step S103.

The above-described processing provides a measure to prevent operation error of the dial in the vicinity by enabling/disabling pulse signal acceptance. Thus, even when the rotary dials are provided close to each other, they can be operated without operation errors.

Third Embodiment

The third embodiment is different from the first embodiment only in the arrangement of the focus dial and the optical vertical movement dial on the joystick, and the control method of the system control unit. Hence, mainly the different points will be described with reference to FIGS. 10 to 12.

Figure 10:
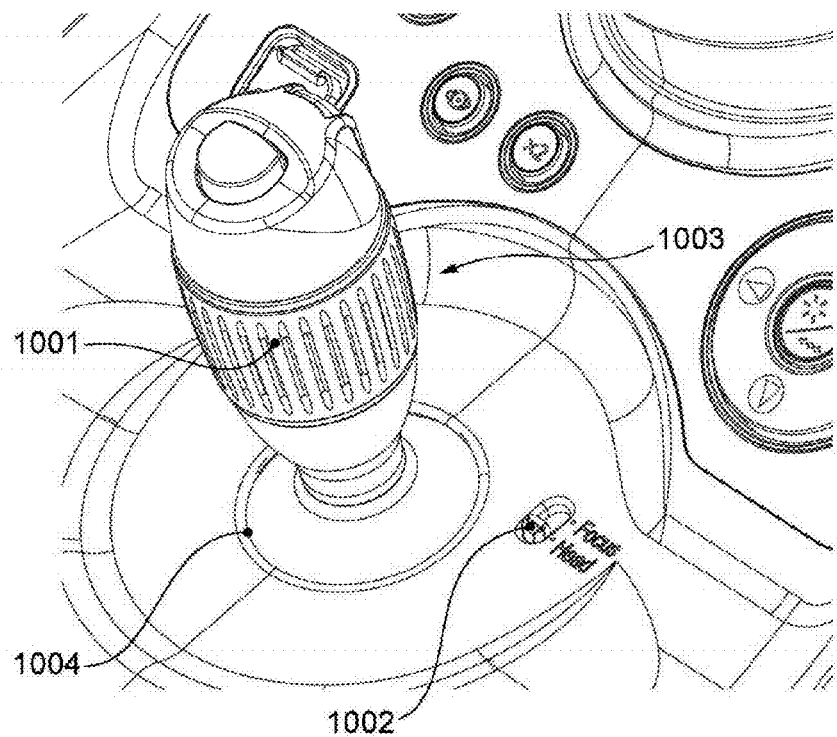
FIG. 10 is a view showing an example of a joystick portion 1003 that constitutes part of a fundus shooting apparatus.
Figure 11:
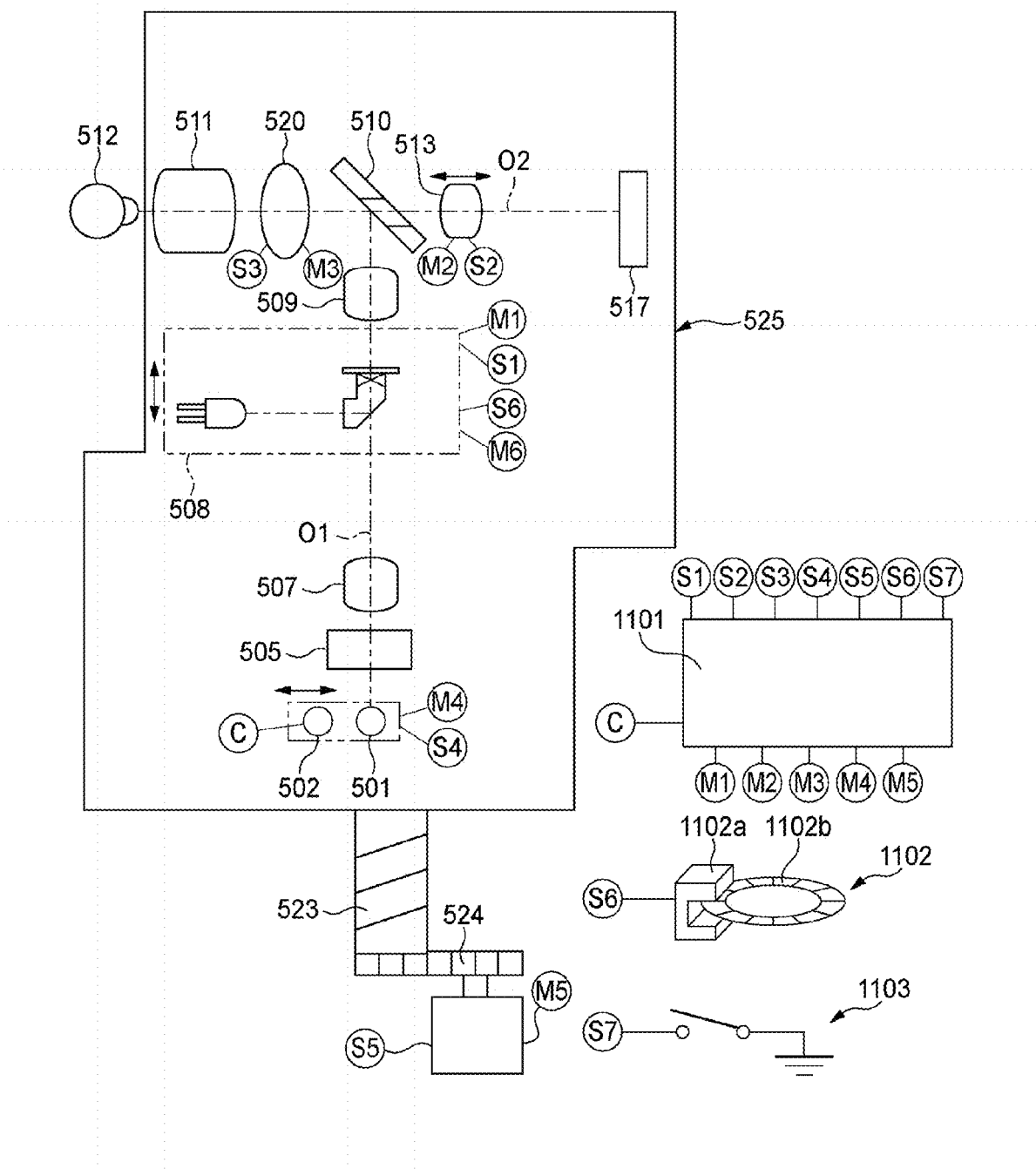
FIG. 11 is a schematic block diagram of a fundus shooting apparatus according to the third embodiment.

A joystick portion 1003 according to the third embodiment will now be described with reference to FIG. 10. A rotary dial 1001 is mechanically linked with a slit plate 1102b of an encoder unit 1102 whose details are illustrated in FIG. 11, and rotates almost coaxially with the central axis of the joystick portion 1003. A switch 1002 changes the mode of the rotary dial 1001. The voltage of a mode switch 1103 shown in FIG. 11 changes upon flipping the switch 1002. A hole 1004 is formed to make the joystick portion 1003 project from the outer cover. In this embodiment, one rotary dial 1001 is arranged. However, a plurality of rotary dials may be arranged, and an operation target may be selected from among them.

When the testing technician operates the rotary dial 1001, the slit plate 1102b passes between the infrared light source portion and the infrared light-receiving element of a photo interrupter 1102a. The encoder unit 1102 sends two pulse signals (not shown) of different timings to a system control unit 1101 through the detection unit S6. The system control unit 1101 detects the rotational direction and the rotating speed from the shift between the two pulses, and adjusts optical unit alignment and focusing. Note that the system control unit 1101 detects the state of the mode switch 1103 through the detection unit S7.

Note that in the third embodiment, the rotary dial is arranged almost coaxially with the joystick. However, the rotary dial may be arranged almost coaxially with the hole 1004 that makes the joystick portion 1003 project from the outer cover, as described in the first embodiment.

Figure 12:
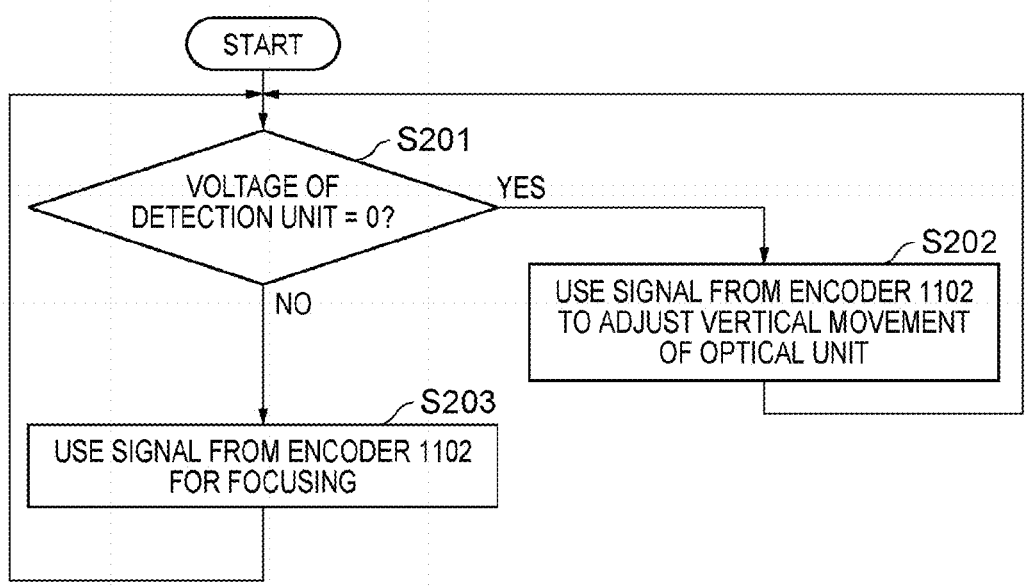
FIG. 12 is a flowchart illustrating the procedure of processing corresponding to the voltage of a detection unit.

The procedure of processing corresponding to the voltage of a detection unit will now be described with reference to the flowchart of FIG. 12. In step S201, the system control unit 1101 determines whether or not the voltage of the detection unit is 0 V. Upon determining that the voltage is 0 V (YES in step S201), the process advances to step S202. Upon determining that the voltage is not 0 V (NO in step S201), the process advances to step S203.

In step S202, the system control unit 1101 uses the signal from the encoder unit 1102 to adjust the vertical movement of an optical unit 525. After that, the process returns to step S201 to continue control until the voltage of the detection unit changes to a voltage other than 0 V.

In step S203, the system control unit 1101 performs control to use the signal from the encoder unit 1102 for focusing. After that, the process returns to step S201 to continue control until the voltage of the detection unit changes to a voltage other than 0 V.

As described above, according to the present invention, it is possible to perform the series of operation from focusing to shooting without changing the position of the hand gripping the joystick. Additionally, without wasteful operations, the shooting time is shorter than before. Furthermore, even if the rotary dials are arranged close to each other, no operation error occurs.

Fourth Embodiment

In the above embodiments, an example has been described in which the joystick mechanism has two rotary dials (the vertical movement dial 102 and the focus dial 101). However, only one of the rotary dials may be arranged.

In the above embodiments, an example has been described in which the operation mechanism of the present invention is applied to an ophthalmic shooting apparatus that shoots a fundus. However, the embodiments of the present invention are not limited to this. The operation mechanism of the present invention is applicable to an ophthalmic apparatus such as a tonometer, a pachymeter, a refractometer, a keratometer, or an auto ref-keratometer. In this case, the shooting unit and the optical unit are replaced with the above-described measuring unit. The position of the measuring unit is adjusted in accordance with the movement of the operation stick, and measurement is performed in accordance with press of a trigger (the shooting button 103 of the first embodiment) arranged on the top of the joystick while being decentered. This makes it possible to reduce operation errors of the testing technician of the ophthalmic apparatus and improve testing efficiency.

According to the present invention, it is possible to perform alignment, focusing, and shooting or measuring operations without changing the grip position on the joystick.

Assigning the function of moving the optical unit in the vertical direction to the rotary dial on the joystick and the focusing function to the rotary dial supported by the supporting member of the operation stick enables the series of operations including alignment, focusing, and shooting or measurement.

During the operation of one of the two rotary dials, control corresponding to the operation of the other is prohibited. This allows a reduction in operation errors that readily occur due to concentration of the operation members near the joystick and greatly improves operability.

When the present invention is applied to an ophthalmic shooting apparatus such as a fundus camera, and the shooting start instruction function is assigned to the trigger, the operability of the ophthalmic shooting apparatus can be improved.

Since the switching button arranged on the operation stick can switch between the anterior ocular segment mode and the fundus shooting mode, operability can further be improved. The switching button is arranged closer to the optical unit than the trigger and can therefore be operated by a finger different from that pressing the trigger while gripping the joystick. It is therefore possible to switch the anterior ocular segment mode and the fundus mode without a large change in the position of the hand of the user gripping the joystick.

The rotary dials are coaxial with the central axis of the operation stick and can be operated by fingers while gripping the joystick.

Since the rotary dials are electrically controlled by the control unit, the force necessary for the rotating operation can be smaller than that for an apparatus having a mechanical rotation detection mechanism. For this reason, even when many operation members such as the trigger and the rotary dials are provided around the joystick, they can be operated by fingers without applying a large force. When the electrical control mechanism is provided, many operation members concentrated around the joystick can be operated without applying a large force. Hence, the operability can be greatly improved.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-195063 filed on Aug. 31, 2010, which is hereby incorporated by reference herein in its entirety.

What is claimed is:

1. An ophthalmic apparatus including an operation stick to adjust an optical unit, comprising:
  a rotary dial that is provided on a side surface of the operation stick and rotates with respect to the operation stick;
  a trigger arranged on a top of the operation stick, said trigger being decentered with respect to the operation stick; and a control unit adapted to control said apparatus to perform one of movement and focusing of the optical unit with respect to an object in accordance with rotation of said rotary dial and to cause the optical unit to start a predetermined operation in accordance with press of said trigger.

2. The apparatus according to claim 1, further comprising:
a supporting member provided at one end of the operation stick; and
another rotary dial supported by said supporting member,
wherein said control unit performs control of said apparatus to move the optical unit with respect to the object in accordance with rotation of said rotary dial provided on the side surface of the operation stick, and to focus in accordance with rotation of the other rotary dial supported by said supporting member.

3. The apparatus according to claim 2, wherein when one of said rotary dial provided on the side surface of the operation stick and said other rotary dial supported by said supporting member is being operated, said control unit does not perform control of said apparatus according to an operation of said rotary dial not currently being operated.

4. The apparatus according to claim 1, wherein
the optical unit is a shooting unit, and
said control unit performs control of said apparatus to cause said shooting unit to start a shooting operation in accordance with press of said trigger.

5. The apparatus according to claim 4, further comprising a switching button arranged on a side surface and the top of the operation stick,
wherein said control unit switches said shooting unit between a mode of observing an anterior ocular segment of the object and a mode of observing a fundus of the object in accordance with press of said switching button.

6. The apparatus according to claim 5, wherein said switching button is arranged on one of the side surface and the top of the operation stick to be closer to the optical unit than said trigger.

7. The apparatus according to claim 1, wherein said rotary dial provided on the side surface of the operation stick is arranged coaxially with a central axis of the operation stick in a longitudinal direction.

8. The apparatus according to claim 1, further comprising:
a driving unit adapted to drive the optical unit; and
a detection unit adapted to detect a rotational direction and a rotating speed of said rotary dial provided on the operation stick,
wherein said control unit controls a driving direction and a driving speed of the optical unit by said driving unit in accordance with the rotational direction and the rotating speed which are detected by said detection unit.

9. The apparatus according to claim 1, wherein when said control unit controls the movement of the optical unit with respect to the object in accordance with rotation of said rotary dial,
said control unit further controls movement of the optical unit, in accordance with tilting of the operation stick, in a direction different from that of the movement according to the rotation of said rotary dial.

10. The apparatus according to claim 1, further comprising a mode switch adapted to change a mode of said rotary dial,
wherein said control unit controls said apparatus to perform the movement and the focusing in accordance with said mode of said rotary dial.

11. An ophthalmic apparatus including a joystick mechanism capable of operating an electric focusing mechanism, comprising:
an operation stick of the joystick mechanism;
at least one rotary dial arranged on at least one of a supporting member provided at one end of said operation stick to support said rotary dial and a side surface of said operation stick; and
a control unit adapted to control focusing by the electric focusing mechanism in accordance with rotation of one said rotary dial.

12. The apparatus according to claim 11, wherein said at least one rotary dial is arranged on one of said operation stick and the supporting member coaxially with a central axis of said operation stick in a longitudinal direction.

13. The apparatus according to claim 11, wherein when the ophthalmic apparatus has a plurality rotary dials,
a first rotary dial is arranged on the side surface of said operation stick, and
a second rotary dial is arranged on the supporting member.

14. The apparatus according to claim 13, further comprising a member that is arranged on said second rotary dial between said second rotary dial and said first rotary dial.

15. An ophthalmic apparatus including an operation stick to adjust an optical unit, comprising:
first and second rotary dials that are provided on a side of the operation stick and rotate with respect to the operation stick; and
a control unit adapted to control movement of the optical unit with respect to an object in accordance with rotation of said first rotary dial and focusing of the optical unit with respect to the object in accordance with rotation of said second rotary dial.

16. The apparatus according to claim 15, further comprising a trigger arranged on a top of the operation stick, said trigger being decentered with respect to the operation stick,
wherein said control unit controls said apparatus to cause the optical unit to start a predetermined operation in accordance with press of said trigger.

17. The apparatus according to claim 15, further comprising a member that is arranged on said second rotary dial between said second rotary dial and said first rotary dial.

18. The apparatus according to claim 15, wherein when one of said first and second rotary dials is operated, said control unit disables any operation of the other of said first and second rotary dials.

19. The apparatus according to claim 15, wherein
the optical unit is a shooting unit, and
said control unit controls said apparatus to cause said shooting unit to start a shooting operation in accordance with press of said trigger.

20. The apparatus according to claim 19, further comprising a switching button arranged on a side surface and the top of the operation stick,
wherein said control unit switches said shooting unit between a mode of observing an anterior ocular segment of the object and a mode of observing a fundus of the object in accordance with press of said switching button.

* * * * *